United States Patent [19]

Herslöf et al.

[11] Patent Number: 5,665,379

[45] Date of Patent: *Sep. 9, 1997

[54] LIPID PARTICLE FORMING MATRIX, PREPARATION AND USE THEREOF

[75] Inventors: Bengt Herslöf, Stockholm; Alf Gunnar Martin Nicklasson, Södertälje, both of Sweden

[73] Assignee: Pharmacia & Upjohn Aktiebolag, Stockholm, Sweden

[ * ] Notice: The term of this patent shall not extend beyond the expiration date of Pat. Nos. 5,626,869 and 5,635,205.

[21] Appl. No.: 242,054

[22] Filed: May 13, 1994

Related U.S. Application Data

[63] Continuation of Ser. No. 859,417, filed as PCT/SE91/00639 Sep. 24, 1991 published as WO92/05771 Apr. 16, 1992, abandoned.

[30] Foreign Application Priority Data

Sep. 28, 1990 [SE] Sweden ................... 9003100

[51] Int. Cl.$^6$ ................... A61K 9/127; A61K 9/14
[52] U.S. Cl. ............ 424/450; 424/484; 424/489; 424/490; 424/498; 424/502; 428/402.2; 264/4.1; 264/4.3
[58] Field of Search ............... 424/450, 484, 424/489, 490, 491, 498, 502; 264/4.1, 4.3; 428/402.2

[56] References Cited

U.S. PATENT DOCUMENTS

| 4,610,868 | 9/1986 | Fountain et al. ................ 424/1.1 |
| 4,877,561 | 10/1989 | Iga et al. ................ 264/4.3 |
| 4,963,367 | 10/1990 | Ecanow ................ 424/455 |

FOREIGN PATENT DOCUMENTS

| 10736/88 | 1/1987 | Australia . |
| 0014 184 B2 | 8/1980 | European Pat. Off. . |
| 0084169A1 | 7/1983 | European Pat. Off. . |
| 0 158 441 A2 | 10/1985 | European Pat. Off. . |
| 0 260 241A1 | 3/1988 | European Pat. Off. . |
| 0260241 | 3/1988 | European Pat. Off. . |
| 3331009A1 | 3/1985 | Germany . |
| 60-7934 | 1/1985 | Japan . |
| WO84/02076 | 6/1984 | WIPO . |
| WO86/05694 | 10/1986 | WIPO . |
| 8707502 | 12/1987 | WIPO . |
| 87/07502 | 12/1987 | WIPO . |
| 93/19736 | 10/1993 | WIPO . |

OTHER PUBLICATIONS

Kim et al., Studies on Liposome–Encapsulated Heparin, Diolog File 154: Medline, 1985–1993.

Kim et al., Studies on Liposome–Encapsulated Heparin, Abstract, Thrombosis Research, vol. 43 (1986), pp. 603–612.

Bates, et al., Bioavailability of Micronized Griseofulvin from Corn Oil–in–Water Emulsion, Aqueous Suspension, and Commercial Tablet Dosage Forms in Humans, Journal of Pharmaceutical Sciences, vol. 64, No. 5, May 1975, pp. 793–797.

Palin, et al., The oral absorption of cefoxitin from oil and emulsion vehicles in rats, International Journal of Pharmaceutics, 33 (1986), pp. 99–104.

Patel, et al., Oral Administration of Insulin by Encapsulation within Liposomes, FEBS Letters, vol. 62, No1. 1 (1976), pp. 60–63.

(List continued on next page.)

Primary Examiner—Gollamudi S. Kishore
Attorney, Agent, or Firm—Pollock, Vande Sande & Priddy

[57] ABSTRACT

The invention relates to a lipid particle forming matrix, characterized by, that from a defined system of at least two lipid components chosen from classes of different polarity, in which at least one of the lipid components is bilayer forming, discrete lipid particles are formed spontaneously when interacting with aqueous systems. Preferably at least one of the lipid components is amphiphatic and polar and one is nonpolar. These discrete particles are formed spontaneously from the matrix without any chemical or physical treatment or initiation. The invention also relates to a process for producing the matrix and use thereof.

40 Claims, 2 Drawing Sheets

OTHER PUBLICATIONS

Flynn, Oral Delivery of Insulin, The Lancet (1989), pp. 1518–1519.

Tarr, et al., Enhanced Intestinal Absorption of Cyclosporine in Rats Through the Reduction of Emulsion Droplet Size, Pharmaceutical Research, vol. 6, No. 1 (1989), pp. 40–43.

Illum, et al., Enhanced nasal absorption of insulin in rats using lysophosphatidylcholine, Int. Jour. of Pharm., 57 (1989), pp. 49–54.

Woolfrey, et al., The effect of Miglyol 8 12 oil on the oral absorption of propranolol in the rat, J. Pharm. Pharmacol., vol. 41 (1989), pp. 579–581.

Winn, et al., The Bioavailability of a Mixed Micellar Preparation of Vitamin $K_1$, and its Procoagulant Effect in Anticoagulated Rabbits, J. Pharm. Pharmacol., vol. 41 (1989), pp. 257–260.

Rowland, et al., The Stability of Liposomes in Vitro to pH, Bile Salts and Pancreatic Lipase, Biochemica et Biophysica Acta, 620 (1980), pp. 400–409.

Manosroi, et al., Thermodynamic Characteristics of a Human Insulin–Deae–Dextran Complex Entrapped in Liposomes, Drug Develop. and Industrial Pharmacy, vol. 16, No. 5 (1990), pp. 837–854.

Weiner, et al., Liposomes as a Drug Delivery System, Drug Devel. and Industrial Pharmacy, vol. 15, No. 10 (1989), pp. 1523–1554.

Payne, et al., Characterization of Proliposomes, Journal of Pharm. Sciences, vol. 75, No. 4, (1986), pp. 330–333.

LIPID PARTICLE FORMING MATRIX, PREPARATION AND USE THEREOF

This application is a continuation, of Ser. No. 07/859,417, filed as PCT/SE91/00639 published as WO92/05771 Apr. 16, 1992, now abandoned.

The present invention relates to lipid matrices which provide the release of bioactive agents through the formation of a type of liposomes in vivo when the matrices interact with water. The spherical lipid bilayers thus formed in vivo, hereinafter referred to as Biosomes (or lipid particle) and the lipid matrix, referred to as a Biosomes Forming Matrix (BFM), should be separated from the well established concept of liposomes or liposome technology which are defined as the formation of lipid vesicles in an aqueous phase or in a freeze-dried form already prepared in vitro before administration. The invention also relates to the production and use of these lipid matrices (BFM).

BACKGROUND

Parenteral depot systems are widely known to those skilled in the art and are well accepted concepts for long term delivery of drugs. These systems are based on biodegradable polymer systems or lipid formulations, e.g. oil solutions and oil suspensions. However, both systems show a serious disadvantage since, after the drug release process has terminated, the lipids or polymer carriers are still at the injection site for a long period of time and, for some systems such as implants, they may even have to be eliminated by surgery. Furthermore, the application of either oils or biodegradable polymers such as polylactic/polyglycolic acid show limited applications since each concept requires specific physicochemical properties of the bioactive material to be included into the systems, e.g. solubility or stability/compatibility.

Hence, parenteral therapy needs a delivery system for bioactive materials applicable for both highly polar as well as nonpolar bioactive materials for which the delivery system shows an intrinsic rate controlling mechanism for drug release, which can be varied over an extensive time frame. A characteristic for such delivery system should be that both the drug release and the biodegradation occur simultaneously.

Since parenteral administration of bioactive materials often needs to be carried out by physicians or nurses and the fact that many people find such therapy uncomfortable, a lot of effort is made on developing drug delivery forms applicable for other routes of administration. Still, the most common route of administration is the enteral (oral, rectal) but during the past decade several attempts have been made to develop intranasal or transdermal delivery systems as alternatives to the parenteral route.

However, the adsorption through biological membranes is a very complex process due to the varying nature of the different membranes to be bypassed as well as the varying nature of the bioactive material used. Many enterally administered drugs also show a high biotransformation when absorbed from the gastrointestinal tract or show a restricted or erratic absorption capacity due to their physicochemical properties, molecular size or sensitivity to degradation processes in the gut, or due to some specific absorption mechanism in limited parts of the gastrointestinal tract. Also, bioactive material administered intranasally or dermally may show erratic and irregular absorption and many delivery formulations hence need the addition of absorption enhancers which in some cases have been shown to be detrimental to the nasal mucosa or the skin due to local side effects.

Due to this lack of regularity, the enteral/nasal/dermal therapy needs a delivery system which eliminates this variability and which is sufficiently flexible for incorporating a variety of bioactive materials, independent of their physicochemical properties, molecular size or source of origin, particularly for such bioactive materials which currently cannot be administered via the enteral route due to limited absorption capacity.

Several papers have been published demonstrating the influence of lipids on drug absorption. However, various results have been obtained showing an enhanced oral absorption either in man or animals, for example:

griseofulvin in an oil-in-water emulsion (Bates and Sequeria, J. Pharm. Sci., 1975, 64, 793), cefoxitin in an oil-in-water emulsion (Palin et al., Int. J. Pharm. 1986, 33, 99), insulin in liposomes of phosphatidylcholine/cholesterol, as well as in water-in-oil microemulsion (Patel and Ryman, FEBS Letters, 1976, 62, 60; Cho and Flynn, Lancet, 1989, Dec. 23/30), cyclosporine in microemulsion (Tarr and Yalkowsky, Pharm. Res. 1989, 6, 4), enhanced nasal absorption in rats of insulin in solution with lysophosphatidylcholine (Illum et al., Int. J. Pharm., 1989, 57, 49).

Decreased absorption was found for propranolol in coconut oil (Palin et al., J. Pharm. Pharmacol., 1989, 41, 579) or no effect at all for vitamin K incorporated into mixed micelles based upon glycolate and lecithin (Winn et al., J. Pharm. Pharmacol., 1989, 41, 257). Furthermore, Rowland and Woodley (Biochim. Biophys. Acta, 1980, 620, 400) have shown that many liposomal systems are quite unstable in the gastrointestinal tract and that drugs incorporated into liposomes gave the same absorption compared to free drug per se. It has recently been indicated in thermodynamic studies, that human insulin-DEAE-dextran complex entrapped in liposomes may present a more stable system than the uncomplexed and/or unentrapped human insulin. However, no evidence that this really works in vivo have been shown (Manosroi et al., Drug Dev. Ind. Pharm., 1990, 16,837).

In some cases there is a therapeutic need to administer bioactive materials locally, such as in wounds after surgery or for the treatment of burns. In those cases, a need exists to deliver the bioactive material locally as well as for an extended period of time in a controllable manner since after surgery no further administration of the formulation is possible, and as in the case of burn injuries, pain may cause severe discomfort to the patient upon repeated administrations. Furthermore, local application to other regions in the body, such as in the vagina, with an extended drug delivery may show therapeutic advantages.

It is well known to those skilled in the art that bioactive materials can be entrapped into unique lipid/aqueous spherical structures defined as liposomes. A liposome is defined as a structure consisting of one or more concentric spheres of lipid bilayers separated by water or aqueous buffer compartments. Thus far, liposome formation and hence manufacturing, has been restricted to techniques where the said formation is carried out in vitro.

Numerous patents and scientific papers on liposomes have been published and the technical field of applying various lipid derivatives in combination with amphiphatic compounds such as phospholipids are well known to those skilled in the art. Liposomes can be prepared by different methods using solvents, reduced pressure, two-phase systems, freeze drying, sonication etc. (Weiner et al., Drug Dev. Ind. Pharm. 1989, 15, 1523).The process technology assigned to these methods is highly complicated. Due to the specific demand in terms of the physicochemical properties of the drug molecule in order to form stable liposome structures, only a limited number of candidate drugs have been shown to be applicable in liposomes formed in vitro. The major application of liposomes have so far been restricted to parenteral delivery and for cosmetic skin care products even though attempts have been made for other routes of administration such as oral, nasal, pulmonary. The applications for parenteral use have been focused on intravenous administration and drug targeting and to some minor extent for extended or controlled release from a depot. Thus far, the applications of liposomes are restricted to the formation and incorporation of bioactive materials in vitro.

A composition for oral delivery of drugs has been disclosed in a patent by Yesair (WO 86/05694), comprising non-esterified fatty acids, monoglycerides with fatty acids having 14–18 carbon atoms, lysophosphatidylcholine in which the fatty acid component has 14–18 carbon atoms and a drug. None Of these single-chained components are bilayer-forming which is a prerequisite for at least one of the lipid components in the present invention.

U.S. Pat. No. 4,610,888 discloses a way of producing liposomes where water-soluble compounds are incorporated. However, this patent deals with globular structures present from the beginning, in contrast to the present invention. The said invention also uses organic solvents in the process which is in contrast to the present invention where the Biosomes are formed spontaneously without any chemical or physical treatment or initiation.

Other documents disclosing the preparation of liposomes are EP 158 441, EP 260 241 and WO 87/07502. According to EP 158 441, in contrast to the present invention, at least one water-miscible liquid (e.g. glycerol, ethanol) and 5–40% water should be added to at least one membrane lipid (e.g. phospholipids such as soy lecithin and egg yolk lecithin. EP 260 241 discloses a dry lipid-based solid material which forms or reconstitutes liposomes in the presence of water. This composition should be dehydrated, e.g. through lyophilization or spray-drying which should not destroy the liposome structure. The liposome structure is thus present from the beginning, in contrast to the present invention. WO 87/07502 discloses a pro-liposome formulation comprising at least one volatile liquid propellant and at least one lipid component. Also in this case discrete particles are formed by dehydration and thus the liposomes are present from the beginning.

The current well known liposome technology, where the systems are prepared in vitro before administration, suffers from the disadvantage that the systems are quite unstable and factors such as temperature or other constituents present in the formulation may dramatically change the nature of the liposomes by irreversibly damaging the bilayers. It is also well known (see Weiner above) that liposomes composed of crude egg yolk phosphatides are not physically stable in vitro at ambient temperatures for more than a few months which limits the application of these formulations in routine practice. By applying the matrix according to the invention the above mentioned stability problems can be avoided.

The above mentioned problems and needs can be met by using a delivery system as described in this application. The present invention, relating to Biosome formation in vivo, will show advantages as compared to already well known lipid drug delivery systems.

The present invention discloses a way to produce, use and/or utilize an entrapment or adsorption procedure for bioactive substances into unique lipid matrices. Such a combination may be used as a pharmaceutical formulation within human and veterinary medicine, in agriculture, or as cosmetic or food/nutritional formulations.

DESCRIPTION OF THE INVENTION

Figure 1:
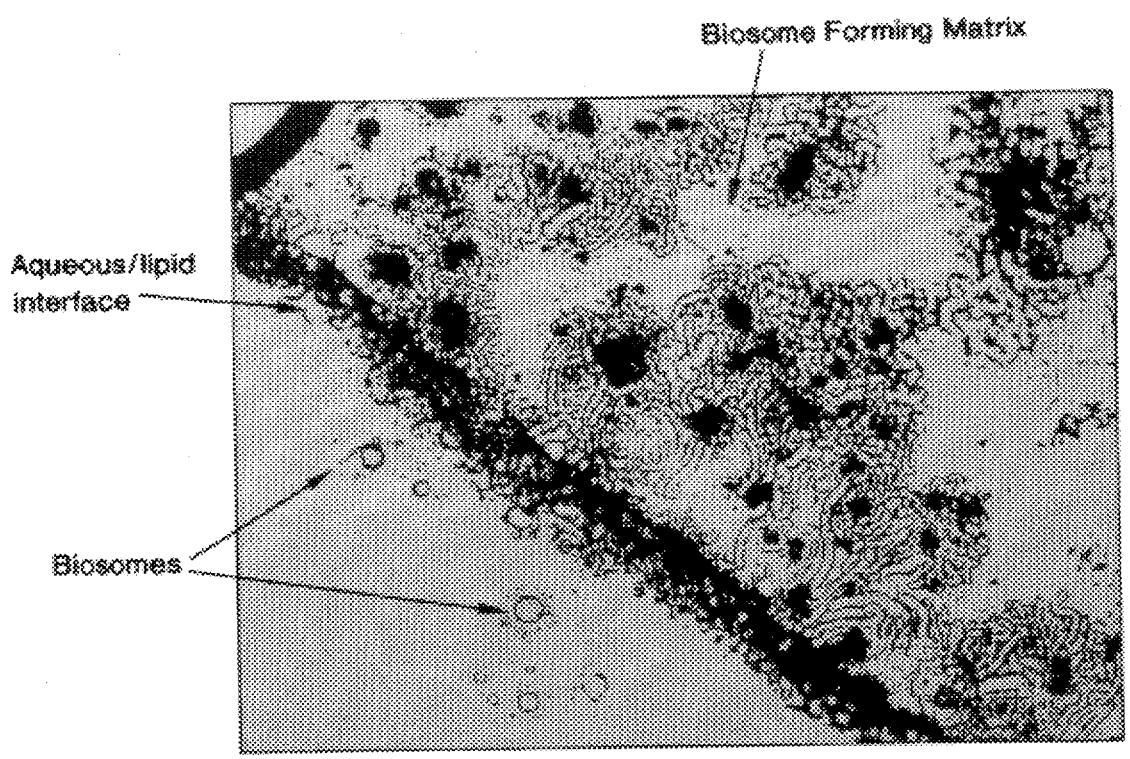
FIG. 1 shows a microscope photo of the formulation according to Example 9.

According to the invention a lipid particle forming matrix is characterized by that from a system of at least two defined lipid components chosen from classes of different polarity, in which at least one of the lipid components is bilayer forming, discrete lipid particles are formed spontaneously when inter-acting with excess aqueous systems. A defined lipid component is a lipid whose chemical composition is known and controlled. In the system at least one of the lipid components is amphiphatic and polar and one is nonpolar.

The amphiphatic and polar component is preferably phosphatidylcholine and the nonpolar lipid is preferably chosen from the classes of mono-, di- and tri- glycerides or a mixture thereof. At room temperature the lipid particle forming matrix has a liquid or semi-solid consistency.

The amount of the polar lipid class components should be in the range of 5–80% (w/w) of the lipid system, preferably in the range of 10–60% (w/w).

The amount of the polar and amphiphatic lipid class components should be in the range of 5–80% (w/w) of the lipid system, preferably in the range of 25–50% (w/w).

Preferably the lipid particle forming matrix contains bioactive materials, which could be chosen from the groups of drugs, herbicides, pesticides, fertilizers, food and cosmetic ingredients or additives. The amount of bioactive material is below 70% (w/w) of the matrix, preferably below 50% (w/w).

In the lipid particle forming matrix the discrete particles are formed spontaneously from the matrix without any chemical or physical treatment or initiation.

When preparing the lipid particle forming matrix the amphiphatic and polar or the nonpolar lipid is mixed with the bioactive material per se, or in solution, and preferably the nonpolar lipid or lipids are admixed to the mixture of the bioactive material and the amphiphatic and polar lipid or lipids.

The lipid particle forming matrix could be used as a carrier system for bioactive materials and especially in pharmaceutical compositions such as oral, rectal, nasal, vaginal, ocular or parenteral vehicles, creams, ointments, capsules and tablets and they could be used for the manufacturing of a pharmaceutical composition for enteral, parenteral, nasal, intravaginal, ocular administration or administration locally on skin, wounds or mucous membranes.

The property 'bilayer forming' is a well-known physical parameter and can easily be established by suitable physicochemical methods (e.g. surface balance method). The establishment of the formed discrete lipid particles can be done by physical and/or chemical methods, such as microscopy using polarized light, or diffraction methods.

The present invention relates to bioactive materials to be entrapped in lipid matrices and will not be restricted to any particular class of bioactive material in terms of physicochemical properties, molecular size or the source of origin, i.e. synthetic, biotechnological materials, etc. The variation in the lipid composition provides the control mechanism by which Biosomes are formed and thereby to the rate of Biosome formation which will serve as a controlling factor for either immediate or sustained release of the entrapped or associated bio-active materials.

The difference between the matrix according to the invention and already known lipid systems, is the capability of spontaneous formation of the Biosomes in contact with excess aqueous media. Thus, by a) using well defined lipid components from at least two different lipid classes and by b) designing these lipid components into unique lipid matrices which form Biosomes in vivo when interacting with water, the system according to the invention can be obtained.

A bioactive material, within the scope of the present invention, is defined in broadest sense, such as a biologically active substance having effect and/or is used within human and/or veterinary medicine, cosmetics as well as within agricultural areas (pesticides, herbicides and/or fertilizers). Also included are areas such as food.

Any type of bioactive agent can be applied. Hence, ibis invention is focused on the principle of lipid particle forming matrices which may contain a bioactive agent where said bioactive agent and hence the Biosome forming matrix design are based upon the physicochemical properties of the various matrix components.

For the person skilled in the art it is obvious that these, substances are not by any means limited to the use within the areas mentioned above, the substances can be, and are used for other purposes or indications than the ones described above. Furthermore, in human and veterinary medicine a pharmacologically active substance, a salt, solvate, enantiomer, or a polymorph thereof may be used, including substances that are synthetic or biosynthetic in their origin. In agricultural areas substances that are used as herbicides or substances that act as stimulators on crop may be used. Also substances that have an effect on various parasites (pesticides) are included. Within the food area the invention may be used to incorporate additives, such as vitamins, preservatives, spices or other taste-carriers in order to protect and/or release such substances in connection with consumption or storage of food.

The following definitions are used:

lipids—a general term for natural or synthetic compounds consisting of acyl carriers, such as glycerol, sphingosine, cholesterol, and others or derivatives thereof, to which one or more fatty acids are or could be linked. Also similar molecules that contains a substantial hydrocarbon portion may be included.

The lipids used for the Biosome Forming Matrices (BFM) can be classified into different lipid classes depending on their polarity, namely:

nonpolar lipid classes—these have no polar head groups. Examples of nonpolar constituents are hydrocarbons, or non-swelling amphiphiles, such as mono-, di- and triacylglycerols, cholesterol, fatty alcohols or cholesterol esters.

polar lipid classes—these have polar head groups and possess surface activity, such as phospholipids or glycolipids. Depending on their specific interactions with water they are further subdivided into the categories of swelling and soluble amphiphiles.

amphiphatic or amphiphilic lipid classes—such as phospholipids and glycolipids, being surface active.

bilayer forming lipid classes—amphiphatic lipids, such as PC (phosphatidyl-chlorine), sphingomyelin, PI (phosphatidylinositol), with a molecular geometry that preferentially leads to bilayer structures in the presence of water.

The lipids used for the BFM consist of a mixture of lipid classes characterized by their different polarities. Polar lipids, such as phospholipids or glycolipids, and nonpolar lipids, such as mono-, di- and triglycerides, are the main constituents in the system but also sterols, such as cholesterol, fatty acids, fatty alcohols and esters thereof as well as other lipid classes may be utilized. This well defined mixture of lipids from different classes as defined above, should not be confused with commercial products such as soybean oil, maize oil or soy lecithin and egg lecithin. To get the well defined lipid classes the commercial material, such as an oil or a lecithin, is fractionated and then the different lipid classes are admixed as explained in more detail in the examples below.

Furthermore, derivatives of lipids may also be used in combination with the above mentioned lipids. One example of this is polyethyleneglycol coupled to phospatidylethanolamine, which has shown to prolong the circulation time of liposomes after injection in the blood stream. Another example of such a derivative is palmitoylcarnitine which acts as an absorption enhancer for bioactive substances in the gut.

In the preferred way of initiating the formation of the BFM, the bioactive substance is admixed to a selected lipid, followed by admixing of a lipid of a different polarity. This polar/nonpolar alteration may be continued for as many cycles as necessary in the specific case, involving a range of lipids with different polarities.

The preferred way of incorporation of a bioactive substance into the BFM is to admix the bioactive substance to amphiphilic lipids in order to create a homogeneous formulation, where the amount of amphiphilic lipids generally is in the total range of 5–80% (w/w). Such an amphiphilic lipid should be capable of spontaneous bilayer formation. Examples thereof are amphiphilic and polar lipid classes, such as phosphatidylcholine, phosphatidylglycerol, phosphatidylinositol or phosphatidylserine or mixtures thereof.

In order to prevent or delay an immediate interaction of the amphiphile(s) with exogenous water, the BFM should also contain one or more nonpolar lipid class. Examples of such nonpolar lipids are mono-, di- or triglycerols, cholesterol or its esters.

Endogenous water, ethanol or other solvents may be present in small amounts (not enough for Biosome formation) in the BFM if the bioactive substance needs such a solvate to be incorporated.

The design of the BFM includes not only the proper selection and/or combination of lipid classes, tailor-made for the solubilization of each bioactive substance, but also the proper selection of the distribution of fatty acids, i.e. the acyl groups attached to the utilized lipid classes. Variation of the acyl groups gives different physicochemical properties as will be seen in the examples below.

By varying the geometrical shape of the main bilayer forming lipid class, i.e. the effective head group area in relation to the steric conformation of the hydrocarbon tails, the rate by which the Biosomes are formed from the BFM in a given aqueous environment can be affected and controlled.

A second way of affecting and controlling the formation of Biosomes is by varying the structure, thus the fluidity, of the hydrocarbon chains in the nonpolar part of the BFM. This will affect the rate of interaction of the endogenous amphiphatic lipids and the exogenous aqueous medium.

Thus, a careful selection of lipid constituents for a specific BFM will be required in order to a) incorporate the bioactive compound in vitro and to b) release the bioactive component by Biosome formation in vivo. This involves the selection of lipid classes as well as the distribution of the fatty acid residues and therefore requires access to analytically pure and well-characterized lipids. The examples below will further illustrate the variation of the matrices by selection of lipids and combinations thereof without limiting the scope of invention.

Thus, the invention relates particularly to the design and behaviour of the BFM which is a new concept for drug delivery of bioactive materials. The invention does not restrict the application of the BFM to any specific route of administration since the BFM will show potential applications for a variety of drug delivery forms such as absorption enhancement of oral, rectal, nasal, dermal formulations or controlled delivery via the parenteral route or locally, e.g. in the vagina or in wounds.

After the formation of the Biosomes in vivo, by means of a controllable rate, drug molecules entrapped into, or associated to the BFM are rapidly liberated once the Biosomes appear in the blood circulation in order for the drug to be able to act pharmacologically. This assumption is supported by the fact that liposomal structures are known to interact rapidly with plasma proteins such as albumin, transferin and macroglobulins, but are also hydrolyzed in vivo by specific phospholipases (Wiener et al., Drug Dev. Ind. Pharm., 1989, 15, 1523). Thus, the use of mortar compounds may be omitted according to the present invention.

According to the present invention, it is possible to incorporate both highly polar as well as nonpolar bioactive materials, in a flexible manner, into a lipid matrix structure by means of a combination of nonpolar lipids and amphiphatic compounds and that these drug containing BFM's form Biosomes, when the BFM's interact with water, thus generating a drug delivery system suitable for either an enhanced or controlled extravascular absorption or a controlled parenteral drug release combined with a biodegradation.

The present invention providers an improved and flexible drug delivery system applicable for various classes of bioactive materials. In vitro release experiments of vitamin B12 (cyanocobolamine) have shown that it is possible to obtain BFM's with different Biosome forming rates as a function of the BFM composition. Furthermore, parenteral drug delivery with controlled release has been found even for highly water-soluble bioactive material such as fragmentated heparin (Fragmin®) using the present invention. Such a combination of a highly hydrophilic bioactive substance with a hydrophobic carrier has hitherto not yet been shown. To those skilled in the art this new and unique property of the present lipid drug delivery carrier (i.e. BFM) must be regarded as highly unpredictable. The results which confirm this are shown in Examples 9, 10 and 15. Also, it has been shown to be possible to incorporate a synthetic low molecular weight substance, i.e. buspirone (cf. Example 22) as well as a high molecular weight compound, i.e. coenzyme Q10 (cf. Example 23).

By incorporating bioactive materials according to the lipid matrix principle in this invention, referred to as Biosome Forming Matrices, the following advantages are obtained compared to conventional pharmaceutical dosage forms, or delivery systems:

a drug delivery system consisting of a lipid matrix and a bioactive material which can be designed in a flexible manner showing a unique capacity for incorporation of either polar or nonpolar bioactive materials showing a wide range of molecular weights without changing the chemical structure and hence the biological activity of the materials.

a drug delivery system consisting of BFM and a bioactive material which forms Biosomes in vivo and for which the rate of Biosome formation can be altered by unique combinations of nonpolar and amphiphatic lipids derivatives.

a drug delivery system consisting of a lipid matrix and a bioactive material which can be used for multipurpose applications such as extravascular absorption enhancement, parenteral controlled drug delivery or local extended drug delivery for which each specific purpose can be achieved by unique lipid combinations in a flexible manner.

a drug delivery system consisting of a lipid matrix and bioactive material which is thermodynamically stable.

a drug delivery system in which the drug and the carrier simultaneously are degraded.

a drug delivery system which gives a possibility to improve the oral administration of high molecular weight compounds such as proteins, peptides, polysaccharides, etc.

This invention relates solely to the concept and design of the novel lipid matrices, the Biosome Forming Matrices, which show a unique formation of Biosomes in vivo after administration, and in which any suitable bioactive material can be incorporated, if needed for any particular reason, such as for improved bioavailability or for extended/controlled release purposes.

Various modifications and equivalents will be apparent to the one skilled in the art and may be used in the compounds, compositions and methods of the present invention without departing from the spirit or scope thereof, and it is therefore to be understood that the invention is not to be limited to the specific examples and embodiments herein.

EXAMPLES

EXAMPLE 1

1.25 g phospholipid from soybean (1) is added to 1.25 g of a glyceride mixture (II) and gently stirred for 12 h at 60° C. 2.50 g of a triglyceride (III) is then added and the total mixture is stirred for 1 h at 60° C.

| Lipid class composition (g) | I | II | III | Fatty acid composition of triacylglycerol (wt %) | |
|---|---|---|---|---|---|
| Phosphatidylcholine | 0.50 | | | | |
| Phosphatidylethanolamine | 0.40 | | | | |
| Phosphatidylinositol | 0.23 | | | | |
| Nonpolar lipids | 0.12 | | | | |
| Monoacylglycerol | | 0.63 | | | |
| Diacylglycerol | | 0.63 | | | |
| Triacylglycerol | | | 2.50 | | |
| | | | | 8:0 caprylate | 58.5 |
| | | | | 10:0 caprate | 40.5 |
| | | | | 12:0 laurate | 0.6 |
| | | | | minors | 0.4 |
| Total | 1.25 | 1.25 | 2.50 | Total | 100 |

EXAMPLE 2

1.25 g phospholipid from soybean (I) is added to 1.25 g of a glyceride mixture (II) and gently stirred for 12 h at 60°

C. 2.50 g of a triglyceride (III) is then added and the total mixture is stirred for 1 h at 60° C.

| Lipid class composition (g) | I | II | III | Fatty acid composition of triacylglycerol (wt %) | |
|---|---|---|---|---|---|
| Phosphatidylcholine | 0.40 | | | | |
| Phosphatidylethanolamine | 0.35 | | | | |
| Phosphatidylinositol | 0.18 | | | | |
| Phosphatidic acid | 0.07 | | | | |
| Nonpolar lipids | 0.25 | | | | |
| Monoacylglycerol | | 0.63 | | | |
| Diacylglycerol | | 0.63 | | | |
| Triacylglycerol | | | 2.50 | | |
| | | | | 8:0 caprylate | 58.5 |
| | | | | 10:0 caprate | 40.5 |
| | | | | 12:0 laurate | 0.6 |
| | | | | minors | 0.4 |
| Total | 1.25 | 1.25 | 2.50 | Total | 100 |

EXAMPLE 3

1.25 g phospholipids from soybean (I) is added to 1.25 g of a glyceride mixture (II) and gently stirred for 12 h at 60° C. 2.50 g of a triglyceride (III) is then added and the total mixture was stirred for 1 h at 60° C.

| Lipid class composition (g) | I | II | III | Fatty acid composition of triacylglycerol (wt %) | |
|---|---|---|---|---|---|
| Phosphatidylcholine | 0.50 | | | | |
| Phosphaltidylethanolamine | 0.40 | | | | |
| Phosphatidylinositol | 0.23 | | | | |
| Nonpolar lipids | 0.12 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 1.25 | 1.25 | 2.50 | Total | 100 |

EXAMPLE 4

1.25 g phospholipid from soybean (I) is added to 1.25 g of a glyceride mixture (II) and gently stirred for 12 h at 60° C. 2.50 of a triglyceride (III) is then added and the total mixture was stirred for 1 h at 60° C.

| Lipid class composition (g) | I | II | III | Fatty acid composition of triacylglycerol (wt %) | |
|---|---|---|---|---|---|
| Phosphatidylcholine | 0.40 | | | | |
| Phosphatidylethanolamine | 0.35 | | | | |
| Phosphatidylinositol | 0.18 | | | | |
| Phosphatidic acid | 0.07 | | | | |
| Nonpolar lipids | 0.25 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 1.25 | 1.25 | 2.50 | Total | 100 |

EXAMPLE 5

1.25 g phospholipid from soybean (I) is added to 1.25 g of a glyceride mixture (II) and gently stirred for 12 h at 60° C.

| Lipid class composition (g) | I | II |
|---|---|---|
| Phosphatidylcholine | 0.40 | |
| Phosphatidylethanolamine | 0.35 | |
| Phosphatidylinositol | 0.18 | |
| Phosphatidic acid | 0.07 | |
| Nonpolar lipids | 0.25 | |
| Monoacylglycerol | | 0.63 |
| Diacylglycerol | | 0.63 |
| Triacylglycerol | | |
| Total | 1.25 | 1.25 |

EXAMPLE 6

1.25 g phospholipid from soybean (I) is added to 1.25 g of a glyceride mixture (II) and 0.16 g ethanol. The total mixture is gently stirred for 6 h at 60° C. 0.16 g of a triglyceride (III) is added and the total mixture is stirred for another hour at the elevated temperature.

| Lipid class composition (g) | I | II | III |
|---|---|---|---|
| Phosphatidylcholine | 0.40 | | |
| Phosphatidylethanolamine | 0.35 | | |
| Phosphatidylinositol | 0.18 | | |
| Phosphatidic acid | 0.07 | | |
| Nonpolar lipids | 0.25 | | |
| Monoacylglycerol | | 0.63 | |
| Diacylglycerol | | 0.63 | |
| Triacylglycerol | | | 0.16 |
| Total | 1.25 | 1.25 | 0.16 |

EXAMPLE 7

15 mg cyanocobalamin (B12) is added to 1.25 g of a glyceride mixture (II) and gently stirred for 3 h at 60° C. 1.25 g phosphatidylcholine from soybean (I) is added and the stirring continues for 6 h at 60° C. 2.50 g of a triglyceride (III) is added and the total mixture is stirred for another hour at the elevated temperature.

| Lipid class composition (g) | I | II | III | Fatty acid composition of triacylglycerol (wt %) |
|---|---|---|---|---|
| Phosphatidylcholine | 1.25 | | | |
| Monoacylglycerol | | 0.63 | | |
| Diacylglycerol | | 0.63 | | |
| Triacylglycerol | | | 2.50 | |

| Lipid class composition (g) | I | II | III | Fatty acid composition of triacylglycerol (wt %) | |
|---|---|---|---|---|---|
| | | | | 8:0 caprylate | 58.5 |
| | | | | 10:0 caprate | 40.5 |
| | | | | 12:0 laurate | 0.6 |
| | | | | minors | 0.4 |
| Total | 1.25 | 1.25 | 2.50 | Total | 100 |

EXAMPLE 8

15 mg cyanocobalamin (B12) is added to 1.25 g of a glyceride mixture (II) and gently stirred for 3 h at 60° C. 1.25 g phosphatidylcholine from soybean(I) is added and the stirring continues for 6 h at 60° C. 2.50 g of a triglyceride (III) is added and the total mixture is stirred for another hour at the elevated temperature.

| Lipid class composition (g) | I | II | III | Fatty acid composition of triacylglycerol (wt %) | |
|---|---|---|---|---|---|
| Phosphatidylcholine | 1.25 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 1.25 | 1.25 | 2.50 | Total | 100 |

Below in Table I, viscosity, melting temperature and melting enthalpy have been measured for the compositions according to Examples 1–8.

TABLE I

| Example | Viscosity (mPa s) | $T_m$ (°C.) | $\Delta H$ (J/g) |
|---|---|---|---|
| 1 | 167 | — | — |
| 2 | 104 | −37.9 | 5.9 |
| | | −3.5 | 50.3 |
| 3 | 199 | −72.1 | 0.7 |
| | | −23.1 | 41.9 |
| 4 | 104 | −72.1 | 0.7 |
| | | −22.2 | 42.0 |
| 5 | 2100 | −17.2 | 18.7 |
| 6 | — | −26.1 | 36.5 |
| | | +6.4 | 14.4 |
| 7 | 133 | | |
| 8 | 900 | | |

Viscosity measured on a Bohlin VOR rheometer at 25° C. $T_m$ (phase transition temperature) and $\Delta H$ (enthalpy change at transition) obtained by means of differential scanning calorimetry.

As can be seen in Table I, various physicochemical properties can be obtained for the BMF's as a function of the lipid combinations used as well as the fatty acid compositions. This will enable the manufacturing of BMF's showing a wide variety of physical properties.

EXAMPLE 9

30 mg cyanocobalamin (B12) is added to 2.50 g of a monoglyceride (II) and the mixture is gently stirred for 3 h at 60° C. 2.50 g phosphatidylcholine from soybean (I) is added and the stirring continues for 6 h at 60° C. 5.00 g of a triglyceride (III) is added and the total mixture is stirred for another hour at the elevated temperature.

| Lipid class composition (g) | I | II | III | Fatty acid composition of triacylglycerol (wt %) | |
|---|---|---|---|---|---|
| Phosphatidylcholine | 2.50 | | | | |
| Monoacylglycerol | | 2.50 | | | |
| Triacylglycerol | | | 5.00 | | |
| | | | | 8:0 caprylate | 58.5 |
| | | | | 10:0 caprate | 40.5 |
| | | | | 12:0 laurate | 0.6 |
| | | | | minors | 0.4 |
| Total | 2.50 | 2.50 | 5.00 | Total | 100 |

EXAMPLE 10

30 mg cyanocobalamin (B12) is added to 2.50 g of a monoglyceride (II) and the mixture is gently stirred for 3 h at 60° C. 2.50 g phosphatidylcholine from soybean (I) is added and the stirring continues for 6 h at 60° C. 5.00 g of a triglyceride (III) is added and the total mixture is stirred for another hour at the elevated temperature.

| Lipid class composition (g) | I | II | III | Fatty acid composition of triacylglycerol (wt %) | |
|---|---|---|---|---|---|
| Phosphatidylcholine | 2.50 | | | | |
| Monoacylglycerol | | 2.50 | | | |
| Triacylglycerol | | | 5.00 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 2.50 | 2.50 | 5.00 | Total | 100 |

FIG. 1 shows a microscope photo of the formulation according to Example 9, 4 min after the addition of external water (magnification=60×). It is apparent from the figure that lipid vesicles, denoted here as Biosomes, are formed from the Biosome Forming Matrix at the interface between aqueous and lipid phase and that the process seems to occur by means of a spontaneous 'budding' mechanism which takes place immediately after contact with external water.

Figure 2:
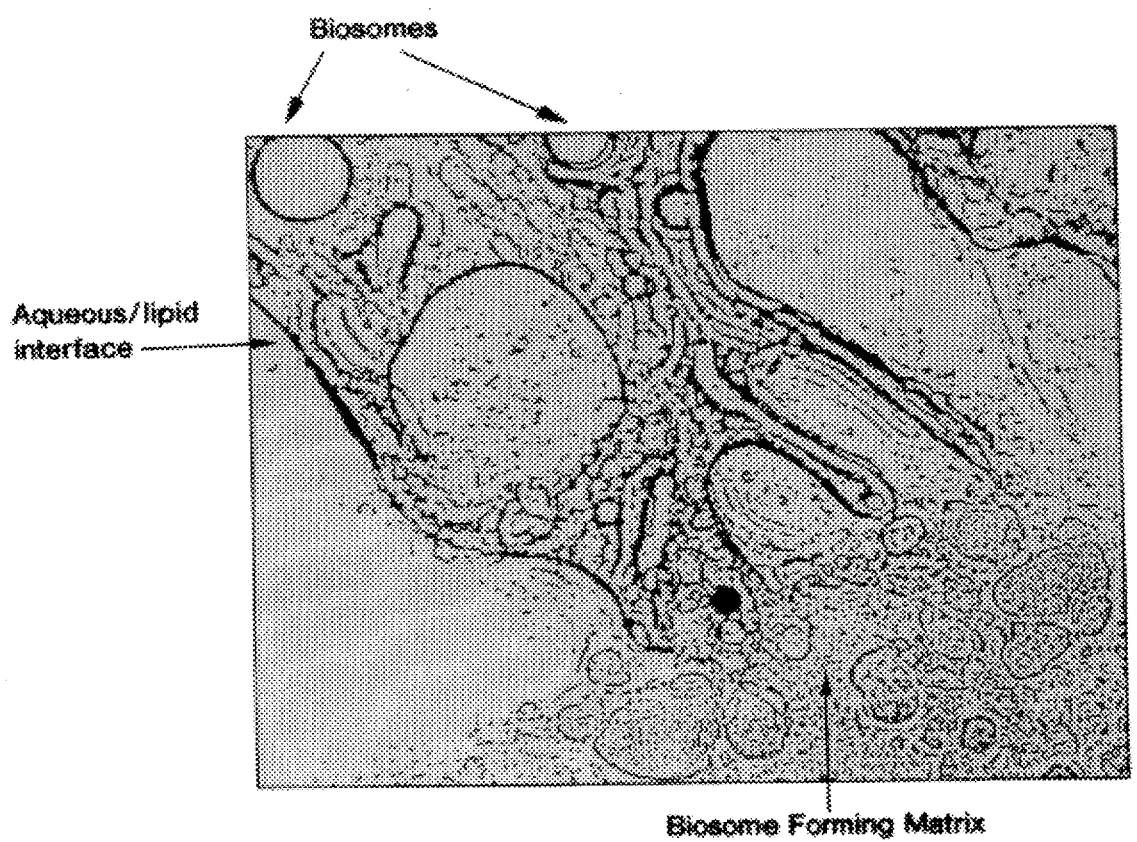
FIG. 2 shows a microscope photo of the formulation according to Example 10.

FIG. 2 shows a microscope photo of the formulation according to Example 10, 10 s after the addition of external water (magnification =60×). As can be seen, worm-like textures are formed in the lipid phase, i.e. the Biosome Forming Matrix, which moves towards the interface between water and lipid. Then at the water-lipid interface, these textures are rapidly transformed by a 'budding' process into spherical lipid vesicles, denoted as Biosomes in this invention.

The in vitro release of vitamin B12 from the BFM's in Examples 9 and 10 was tested. The BMF formulations were added to water at 20° C. and then shaken gently for 3 min before measuring the B12 concentration in the aqueous phase. The formulations were allowed to stand for 120 min followed by a repeated analysis. In order to obtain a clear aqueous phase, centrifugation was performed for 30 min at 45,000 rpm before concentration measurements. The results are shown in Table II.

TABLE II

| | Release | |
|---|---|---|
| Time (min) | Example 9 | Example 10 |
| 3 | 85% | 76% |
| 120 | 85% | 84% |

As can be seen, a very rapid and spontaneous release of vitamin B12 was obtained from the two BFM formulations. Also, depending on the lipid composition different release properties were obtained. Only small changes in the fatty acid composition gave different release properties. The lipid particles according to the experiment given in Table II above, i.e. Biosomes formed from Examples 9 and 10, were subjected to size analysis using a Malvern equipment. The results thus obtained are shown in Table III.

TABLE III

| Example No. | Time (min) | Size | |
|---|---|---|---|
| 9 | 3 | 26% <1 μm | >1 μm 66% <2 μm |
| | 120 | 41% <1 μm | >1 μm 46% <2 μm |
| 10 | 3 | 0% <1 μm | >1 μm 96% <10 μm |
| | 120 | 44% <1 μm | >1 μm 52% <2 μm |

Initially, smaller Biosomes are spontaneously formed for Example 9 compared to Example 10 as evident from Table III. Furthermore, for the smaller Biosome forming matrices a more rapid drug release can be seen, cf. Table II. Another interesting phenomenon can be seen in Table III in terms of the time for the formation of smaller Biosomes. A longer lag time for this process was found for Example 10 compared to Example 9 which demonstrated the possibility of controlling this process by means of lipid composition in the BFM's.

EXAMPLE 11

2.50 g phosphatidylcholine from soybean (I) and 7.50 g of a monoglyceride (II) are gently stirred for 6 h at 60° C. 1.25 g water is added and the stirring continues for another hour at the elevated temperature.

| Lipid class composition (g) | I | II |
|---|---|---|
| Phosphatidylcholine | 2.50 | |
| Monoacylglycerol | | 7.50 |
| Total | 2.50 | 7.50 |

EXAMPLE 12

2.50 g phosphatidylcholine from soybean (I) and 7.50 g of a monoglyceride are gently stirred for 6 h at 60° C. 1.25 g Fragmin® solution (120 mg/g water) is added and the stirring continues for another hour at the elevated temperature.

| Lipid class composition (g) | I | II |
|---|---|---|
| Phosphatidylcholine | 2.50 | |
| Monoacylglycerol | | 7.50 |
| Total | 2.50 | 7.50 |

EXAMPLE 13

2.50 g phosphatidylcholine from soybean (I) and 7.50 g of a monoglyceride are gently stirred at 60° C. for 6 h. 0.625 g Fragmin® solution (120 mg/g water) is added and the stirring continues for another hour at the elevated temperature.

| Lipid class composition (g) | I | II | Fatty acid composition of monoacyl-glycerol (wt %) | |
|---|---|---|---|---|
| Phosphatidylcholine | 2.50 | | | |
| Monoacylglycerol | | 7.50 | | |
| | | | 8:0 caprylate | 79.6 |
| | | | 10:0 caprate | 19.8 |
| | | | 12:0 laurate | 0.2 |
| | | | minors | 0.4 |
| Total | 2.50 | 7.50 | Total | 100 |

EXAMPLE 14

2.50 g phosphatidylcholine from soybean (I) and 7.50 g of a monoglyceride (II) are gently stirred at 60° C. for 6 h. 1.25 g Fragmin® solution (120 mg/g water) is added and the stirring continues for another hour at the elevated temperature.

| Lipid class composition (g) | I | II | Fatty acid composition of monoacyl-glycerol (wt %) | |
|---|---|---|---|---|
| Phosphatidylcholine | 2.50 | | | |
| Monoacylglycerol | | 7.50 | | |
| | | | 8:0 caprylate | 78.4 |
| | | | 10:0 caprate | 21.2 |
| | | | 12:0 laurate | 0.2 |
| | | | minors | 0.2 |
| Total | 2.50 | 7.50 | Total | 100 |

EXAMPLE 15

2.50 g phosphatidylcholine from soybean (I) and 7.50 g of a monoglyceride (II) are gently stirred at 60° C. for 6 h. 0.625 g Fragmin® solution (120 mg/g water) is added and the stirring continues for another hour at the elevated temperature.

| Lipid class composition (g) | I | II | Fatty acid composition of monoacyl-glycerol (wt %) | |
|---|---|---|---|---|
| Phosphatidylcholine | 2.50 | | | |
| Monoacylglycerol | | 7.50 | | |
| | | | 8:0 caprylate | 78.4 |
| | | | 10:0 caprate | 21.2 |
| | | | 12:0 laurate | 0.2 |
| | | | minors | 0.2 |
| Total | 2.50 | 7.50 | Total | 100 |

The size distribution of the Biosomes formed in water at 37° C. was determined for Example 15 using a Malvern equipment. The BFM formulation was shaken gently in water for 17 h followed by centrifugation in order to separate the lipid phase from the aqueous phase. The result is shown in Table IV.

TABLE IV

| Size | % |
|---|---|
| <1 μm | 36 |
| >1 μm, <2 μm | 60 |

Example 15 was also administered in a rabbit by subcutaneous injection. Blood samples were collected and the plasma concentration of Fragmin® was analyzed as a function of time. The results are shown in Table V.

TABLE V

| Time (h) | Fragmin® plasma concentration (IU/ml) |
|---|---|
| 0 | 0 |
| 1.0 | 0 |
| 2.0 | 0 |
| 2.5 | 0.051 |
| 3.0 | 0.100 |
| 3.5 | 0.110 |
| 4.0 | 0.127 |
| 4.5 | 0.130 |
| 5.0 | 0.122 |
| 5.5 | 0.126 |
| 6.0 | 0.133 |
| 7.0 | 0.126 |

As can be seen in Table V, a constant and extended release of Fragmin® was obtained in vivo. It seems as if it is now possible to deliver in vivo a highly water-soluble high molecular weight compound at a constant rate by means of the present invention.

Examples 16–23 show various formulations based on the present invention demonstrating the flexibility of said invention. The examples show that it is possible to incorporate both highly complex molecules such as vitamin B12 as well as low molecular weight compound, e.g. buspirone and high molecular weight molecules, e.g. fragmentated heparin (Fragmin®) where each bioactive compound possesses different physicochemical properties.

EXAMPLE 18

150 mg cyanocobalamin (B12) is added to 12.50 g of a monoglyceride (II) and the mixture is gently stirred at 60° C. for 3 h. 12.50 g phosphatidylcholine from soybean (I) is added and the stirring continues for 6 h at 60° C. 25.00 g of a triglyceride (III) is added and the total mixture is stirred for another hour at the elevated temperature.

| Lipid class composition (g) | I | II | III | Fatty acid composition of triacyl-glycerol (wt %) | |
|---|---|---|---|---|---|
| Phosphatidylcholine | 12.50 | | | | |
| Monoacylglycerol | | 12.50 | | | |
| Triacylglycerol | | | 25.00 | | |
| | | | | 8:0 caprylate | 58.5 |
| | | | | 10:0 caprate | 40.5 |
| | | | | 12:0 laurate | 0.6 |
| | | | | minors | 0.4 |
| Total | 12.50 | 12.50 | 25.00 | Total | 100 |

EXAMPLE 17

150 mg cyanocobalamin (B12) is added to 12.50 g of a monoglyceride (II) and the mixture is gently stirred at 60° C. for 3 h. 12.50 g phosphatidylcholine from soybean (I) is added and the stirring continues for 6h. at 60° C. 25.00 g of a triglyceride (III) is added and the total mixture is stirred for another hour at the elevated temperature.

| Lipid class composition (g) | I | II | III | Fatty acid composition of triacyl-glycerol (wt %) | |
|---|---|---|---|---|---|
| Phosphatidylcholine | 12.50 | | | | |
| Monoacylglycerol | | 12.50 | | | |
| Triacylglycerol | | | 25.00 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 12.50 | 12.50 | 25.00 | Total | 100 |

EXAMPLE 18

150 mg cyanocobalamin (B12) is added to 33.30 g of a monoglyceride (II) and the mixture is gently stirred at 60° C. for 3 h. 11.10 g phosphatidylcholine from soybean (I) is added and the stirring continues for 6 h at 60° C. 5.60 g of water is added and the total mixture is stirred for another hour at the elevated temperature.

| Lipid class composition (g) | I | II |
|---|---|---|
| Phosphatidylcholine | 11.10 | |
| Monoacylglycerol | | 33.30 |
| Triacylglycerol | — | — |
| Total | 11.10 | 33.30 |

EXAMPLE 19

15 mg cyanohydroxycobalamin acetate is added to 1.25 g of a glyceride mixture (II) and gently stirred at 60° C. for 3 h. 1.25 g phosphatidylcholine from soybean (I) is added and the stirring continues for 6 h at 60° C. 2.50 g of a triglyceride (III) is added and the total mixture is stirred for another hour at the elevated temperature.

| Lipid class composition (g) | I | II | III | Fatty acid composition of triacylglycerol (wt %) | |
|---|---|---|---|---|---|
| Phosphatidylcholine | 1.25 | | | | |
| Monoacylglycerol | | 0.63 | | | |
| Diacylglycerol | | 0.63 | | | |
| Triacylglycerol | | | 2.50 | | |
| | | | | 8:0 caprylate | 58.5 |
| | | | | 10:0 caprate | 40.5 |
| | | | | 12:0 laurate | 0.6 |
| | | | | minors | 0.4 |
| Total | 1.25 | 1.25 | 2.50 | Total | 100 |

EXAMPLE 20

15 mg cyanohydroxycobalamin acetate is added to 1.25 g of a glyceride mixture (II) and gently stirred at 60° C. for 3 h. 1.25 g phosphatidylcholine from soybean (I) is added and the stirring continues for 6 h at 60° C. 2.50 g of a triglyceride (III) is added and the total mixture is stirred for another hour at the elevated temperature.

| Lipid class composition (g) | I | II | III | Fatty acid composition of triacylglycerol (wt %) | |
|---|---|---|---|---|---|
| Phosphatidylcholine | 1.25 | | | | |
| Monoacylglycerol | | 0.63 | | | |
| Diacylglycerol | | 0.63 | | | |
| Triacylglycerol | | | 2.50 | | |
| | | | | 16:0 palmitate | 10.0 |
| | | | | 18:0 sterarate | 2.8 |
| | | | | 18:1 oleate | 20.6 |
| | | | | 18:2 linoleate | 58.9 |
| | | | | 18:3 linolenate | 6.7 |
| | | | | minors | 1.0 |
| Total | 1.25 | 1.25 | 2.50 | Total | 100 |

EXAMPLE 21

2.50 g phosphatidylcholine from soybean (I) and 7.50 g of a monoglyceride (II) are gently stirred for 6 h at 60° C. 2.0 ml Fragmin® solution (334 mg/g water) is added and the stirring continues for another hour at the elevated temperature.

| Lipid class composition (g) | I | II |
|---|---|---|
| Phosphatidylcholine | 2.50 | |
| Monoacylglycerol | | 7.50 |
| Total | 2.50 | 7.50 |

EXAMPLE 22

10 mg buspirone hydrochloride is added to 50 mg of a monoglyceride (II) and the mixture is gently stirred for 1 h at 60° C. 200 mg of a diglyceride (III) and 250 mg phosphatidylcholine from soybean (I) is added and the stirring continues for 3 h at 60° C. 500 mg of a triglyceride (IV) is added and the total mixture is stirred for another 10 min at the elevated temperature.

| Lipid class composition (mg) | I | II | III | IV | Fatty acid composition of triacylglycerol (wt %) | |
|---|---|---|---|---|---|---|
| Phosphatidylcholine | 250 | | | | | |
| Monoacylglycerol | | 50 | | | | |
| Diacylglycerol | | | 200 | | | |
| Triacylglycerol | | | | 500 | | |
| | | | | | 8:0 caprylate | 58.5 |
| | | | | | 10:0 caprate | 40.5 |
| | | | | | 12:0 laurate | 0.6 |
| | | | | | minors | 0.4 |
| Total | 250 | 50 | 200 | 500 | Total | 100 |

EXAMPLE 23

20 mg coenzyme Q10 is added to 200 mg of a diglyceride (II) and 250 mg phosphatidylcholine from soybean (I) and the mixture is gently stirred for 6 h at 60° C. 500 mg of a triglyceride (III) is added and the total mixture is stirred for another hour at the elevated temperature.

| Lipid class composition (mg) | I | II | III | Fatty acid composition of triacylglycerol (wt %) | |
|---|---|---|---|---|---|
| Phosphatidylcholine | 250 | | | | |
| Diacylglycerol | | 200 | | | |
| Triacylglycerol | | | 500 | | |
| | | | | 8:0 caprylate | 58.5 |
| | | | | 10:0 caprate | 40.5 |
| | | | | 12:0 laurate | 0.6 |
| | | | | minors | 0.4 |
| Total | 250 | 200 | 500 | Total | 100 |

We claim:

1. An essentially water-free, liquid or semi-solid, lipid particle forming matrix comprising a bioactive material and a system of analytically pure lipids comprising at least two lipids of different polarity, wherein
    i) at least one lipid is phosphatidylcholine, which is a polar and amphiphilic bilayer forming phospholipid in an amount of 5 to 50% (w/w) of the lipids, and, the remainder of said system is,
    ii) at least one lipid that is a nonpolar lipid and comprises a mixture of monoacyl glycerols wherein the acyl group of each is selected from the group consisting of caprylate (C:8) and caprate (C:10), and
    wherein the said composition forms discrete lipid particles spontaneously at the interface between aqueous and lipid phase after contact with external water of an aqueous medium by budding.

2. A pharmaceutical composition for enteral, nasal, intravaginal, ocular or parenteral administration or administration locally on skin, wounds or mucous membranes containing the matrix for bioactive materials according to claim 1 and optionally suitable carriers and solvents for dissolving the bioactive materials.

3. Composition according to claim 2 wherein the nonpolar lipid components contain a triacyl glycerol with essentially a mixture of caprylate (8:0) and caprate (10:0), as the acyl groups.

4. Composition according to claim 2 wherein the nonpolar lipid component contains a triacyl glycerol with essentially a mixture of oleate (18:1) and palmitate (16:0), as the acyl groups.

5. Composition according to claim 2 wherein the nonpolar lipid components contain a triacyl glycerol with essentially a mixture of caprylate (C:8) and caprate (C:10) as the acyl groups.

6. Composition according to claim 2 wherein said polar and amphiphilic bilayer forming components are present in an amount of 25–50% of (w/w) of the lipids.

7. Composition according to claim 6 wherein the polar, and amphiphilic bilayer forming lipid components is phosphatidylcholine in an amount of 50% of the lipids.

8. Composition according to claim 2 wherein the bioactive material is selected from the group consisting of drugs, herbicides, pesticides, fertilizers, food components and cosmetics ingredients.

9. Composition according to claim 8, which further contains a solvent for dissolving the bioactive material and wherein the amount of said solvent is smaller than that necessary for formation of lipid particles.

10. Composition according to claim 9 wherein said solvent is water or ethanol.

11. Composition according to claim 9 wherein the amount of bioactive material is below 70% (w/w) of the matrix.

12. Matrix according to claim 2 wherein the said polar and amphiphilic bilayer forming components is present in an amount of 10 to 50% (w/w) of the lipids.

13. A process for preparing the matrix according to claim 1 characterized by mixing the polar and amphiphilic bilayer forming lipid or the nonpolar lipid is mixed with the bioactive material per se or in solution.

14. A process according to claim 13 characterized by a first admixing of the nonpolar lipid or lipids with the bioactive material and thereafter admixing with the polar and amphiphilic lipid or lipids.

15. The composition of claim 2 which contains water as a solvent.

16. A process for forming lipid carrier particles from an essentially water-free, liquid or semi-solid matrix consisting essentially of mixing, in arbitrary order, i) analytically pure phospholipid selected from the group consisting of phosphatidylcholine, phosphatidylglycerol, phosphatidylinositol, phosphatidylserine, phosphatidyl ethanolamine, phosphatidic acid, and derivatives and mixtures thereof which is a polar and amphiphilic bilayer forming phospholipid in an amount of 5 to 50% (w/w) of the lipids, ii) at least one analytically pure nonpolar lipid and comprises a mixture of monoacyl glycerols wherein the acyl group of each is selected from the group consisting of caprylate (C:8) and caprate (C:10), as the remainder of the lipid, and iii) a bioactive material, whereupon external water or an aqueous medium is added at which discrete lipid particles are formed spontaneously at the interface between the aqueous and lipid phase by budding.

17. A process according to claim 16, wherein the nonpolar lipid component or the polar and amphipihilic lipid component is first mixed with the bioactive material per se or in solution, and thereafter mixed with the remaining lipid component.

18. A process according to claim 17, wherein the nonpolar lipid component is first mixed with the bioactive material, and thereafter mixed with the polar and amphiphilic lipid component.

19. Composition according to claim 16 wherein the amount of bioactive material is below 50% (w/w) of the matrix.

20. Composition according to claim 1 wherein the nonpolar lipid components contain a triacyl glycerol with essentially caprylate (8:0) and caprate (10:0) as the acyl groups.

21. Composition according to claim 1 wherein the nonpolar lipid component contains a triacyl glycerol with essentially oleate (18:1) and palmitate (16:0) as the acyl groups.

22. Composition according to claim 1 wherein the nonpolar lipid component contains a monoacyl glycerol with essentially caprylate (8:0) and caprate (10:0) as the acyl groups.

23. Composition according to claim 1 wherein said polar and amphiphilic bilayer forming component is are present in an amount of 25–50% of (w/w) of the lipids.

24. Composition according to claim 23 wherein the polar and amphiphilic bilayer forming lipid component is phosphatidylcholine in an amount of 50% of the lipids.

25. Composition according to claim 1 wherein the bioactive material is selected from the group consisting of drugs, herbicides, pesticides, fertilizers, foods and cosmetic ingredients.

26. Composition according to claim 25 which further contains a solvent for dissolving the bioactive material and wherein the amount of said solvent is smaller than that necessary for formation of lipid particles.

27. Composition according to claim 26 wherein said solvent is water or ethanol.

28. Composition according to claim 26 wherein the amount of bioactive material is below 70% (w/w) of the matrix.

29. Composition according to claim 26 wherein the amount of bioactive material is below 50% (w/w) of the matrix.

30. Composition according to claim 1 wherein the said polar and amphiphilic bilayer forming component is present in an amount of 10 to 50% (w/w) of the lipids.

31. A process for preparing the matrix according to claim 1 characterized by mixing one of the phosphatidylcholine or the nonpolar lipid with the bioactive material per se or with a solution of the bioactive material and then mixing with the other of the phosphatidylcholine or the nonpolar lipid.

32. A process according to claim 31 characterized by a first admixing of the nonpolar lipid or lipids with the bioactive material and thereafter admixing with the polar and amphiphilic lipid or lipids.

33. Composition according to claim 1, wherein the lipids are purified by fractionation.

34. Composition according to claim 1, wherein the discrete lipid particles are (essentially) spherical.

35. Composition according to claim 1, wherein the bioactive material is highly water-soluble.

36. Composition according to claim 35, wherein the highly water-soluble bioactive material is fragmentated heparin.

37. Process according to claim 16, wherein the lipids are purified by fractionation.

38. Process according to claim 16, wherein the discrete lipid particles are (essentially) spherical.

39. Process according to claim 16, wherein the bioactive material is highly water-soluble.

40. Process according to claim 16, wherein the highly water-soluble bioactive material is fragmentated heparin.

* * * * *